(12) United States Patent
Hill et al.

(10) Patent No.: US 12,713,208 B2
(45) Date of Patent: Aug. 18, 2026

(54) DEVICE FOR TRACKING A PERSON BY USING CONTEXTUALISED ACTIVITY MEASUREMENTS

(71) Applicant: Panoramic Digital Health, Saint-Pierre de Chartreuse (FR)

(72) Inventors: Derek Hill, Saint-Pierre-de-Chartreuse (FR); Nicolas Defranoux, Saint-Pierre de Chartreuse (FR)

(73) Assignee: Panoramic Digital Health, Saint-Pierre-de-Chartreuse (FR)

( * ) Notice: Subject to any disclaimer, the term of this patent is extended or adjusted under 35 U.S.C. 154(b) by 262 days.

(21) Appl. No.: 18/550,507

(22) PCT Filed: Mar. 13, 2022

(86) PCT No.: PCT/EP2022/056419
§ 371 (c)(1),
(2) Date: Sep. 14, 2023

(87) PCT Pub. No.: WO2022/194719
PCT Pub. Date: Sep. 22, 2022

(65) Prior Publication Data

US 2024/0163643 A1 May 16, 2024

(30) Foreign Application Priority Data

Mar. 14, 2021 (FR) ...................................... 2102508

(51) Int. Cl.
*H04W 4/029* (2018.01)
*A61B 5/11* (2006.01)
*H04W 4/80* (2018.01)

(52) U.S. Cl.
CPC ........... *H04W 4/029* (2018.02); *A61B 5/1118* (2013.01); *H04W 4/80* (2018.02)

(58) Field of Classification Search
CPC .................................................... H04W 4/029
(Continued)

(56) References Cited

U.S. PATENT DOCUMENTS

2011/0105862 A1* 5/2011 Gies .................... A61B 5/1126 600/301
2016/0317067 A1* 11/2016 Lee ..................... A61B 5/1123
(Continued)

FOREIGN PATENT DOCUMENTS

WO 2020/198090 A1 10/2020

OTHER PUBLICATIONS

International Search Report for International Application No. PCT/EP2022/056419, mailed Jun. 22, 2022, 5 pages with English translation.

(Continued)

*Primary Examiner* — Qutbuddin Ghulamali
(74) *Attorney, Agent, or Firm* — TraskBritt

(57) ABSTRACT

A device, for monitoring the status of a user in an environment, includes a mobile module intended to be worn by the user. The mobile module includes an activity sensor and a processing unit. The processing unit is for establishing a status signal from an activity signal generated by the activity sensor. The device also includes beacons distributed in the environment. The beacons are configured to send a transmission signal to the mobile module via a short-range wireless connection. The processing unit is configured to establish a position signal as a function of at least one distance between the mobile module and a beacon. The transmission unit is configured to transmit the status signal and the position signal to a central unit.

20 Claims, 11 Drawing Sheets

(58) Field of Classification Search
USPC ........................................................ 455/456.1
See application file for complete search history.

(56) References Cited

U.S. PATENT DOCUMENTS

| | | | | |
|---|---|---|---|---|
| 2016/0379476 | A1 * | 12/2016 | Sella .................. | G08B 21/0492 340/539.19 |
| 2022/0003831 | A1 * | 1/2022 | de Jong .................. | A45F 5/021 |
| 2022/0039673 | A1 * | 2/2022 | Sobol ................. | A61B 5/02055 |

OTHER PUBLICATIONS

International Written Opinion for International Application No. PCT/EP2022/056419, mailed Jun. 22, 2022, 14 pages with English machine translation.

* cited by examiner ms
1
2

DEVICE FOR TRACKING A PERSON BY USING CONTEXTUALISED ACTIVITY MEASUREMENTS

CROSS-REFERENCE TO RELATED APPLICATIONS

This application is a national phase entry under 35 U.S.C. § 371 of International Patent Application PCT/EP2022/056419, filed Mar. 13, 2022, designating the United States of America and published as International Patent Publication WO 2022/194719 A1 on Sep. 22, 2022, which claims the benefit under Article 8 of the Patent Cooperation Treaty to French Patent Application Serial No. FR2102508, filed Mar. 14, 2021.

TECHNICAL FIELD

The technical field of the disclosure is that of monitoring an individual using measurements of activities undertaken by the individual coupled with position information of the individual inside a building.

BACKGROUND

Current connected objects benefit from connectivity technologies that can be used in health-related applications. An example of a recent application relates to applications for detecting proximity with an individual who subsequently proves to be contaminated with a virus. This type of application has proved to be particularly effective in the countries where it was widely used, for example, in South Korea.

Furthermore, there is an increasing demand for home care, with this demand originating both from patients and health authorities, in order to optimize the time spent in a hospital environment. Keeping some sick individuals, or those suffering from a handicap, or who are elderly, at home, or in non-hospital infrastructures, assumes that appropriate monitoring has been contemplated. The rapid development of connected devices is currently being seen, allowing data related to the physical or physiological activity of individuals to be transmitted from their place of residence, whether it is a private dwelling or a specialized home structure.

It is also known that conventional geolocation systems, for example, of the GPS type, can lack reliability when inside a building. In addition, the consumption of this type of device is high, which requires a high-capacity battery or frequent recharging. To date, the location information of an individual is seldom used in devices allowing the physiological data of an individual to be transmitted.

Documents US 2016/0379476 and WO 2020/198090 describe devices intended to be worn by an individual, with the aim of monitoring the activity undertaken by the individual, in particular in the home.

BRIEF SUMMARY

Embodiments of the disclosure fall within the above-described context. Proposed is an improved device, the implementation of which allows remote monitoring of a change in the status of a user and takes into account the user's position, in particular the position inside a building.

A first aim of embodiments of the disclosure is a device for monitoring the status of a user, with the user occupying an environment, the device comprising:

a mobile module, intended to be worn by the user; and beacons, distributed in the environment, configured to send a transmission signal to the mobile module via a short-range wireless connection;

the mobile module comprising:

a short-range wireless connection unit, configured to receive at least one transmission signal transmitted by at least one beacon, and preferably a plurality of transmission signals respectively transmitted by a plurality of beacons;

a range-finding unit, configured to estimate, at different measurement times, a distance between the mobile module and each beacon whose transmission signal is received by the mobile module;

at least one activity sensor of the user, configured to establish an activity signal representing an activity of the user at each measurement time;

a processing unit, configured to generate a status signal from at least one activity signal measured by the activity sensor; and a transmission unit, configured to transmit the status signal to a central unit;

the device being characterized in that:

the processing unit is configured to establish a position signal as a function of at least one distance estimated by the range-finding unit, at each measurement time, with the position signal representing a position of the user relative to the environment; and the transmission unit is configured to transmit the status signal and the established position signal, at each measurement time, to the central unit, so as to allow the central unit to record the status signal and the established position signal at each measurement time.

The activity sensor can comprise at least:

a motion sensor; and/or a cardiac activity sensor; and/or a muscle activity sensor; and/or a brain activity sensor; and/or a blood pressure sensor; and/or an analyte sensor.

According to one embodiment, at least one beacon is a privacy beacon, the device being programmed such that when the mobile module receiving a transmission signal transmitted by the privacy beacon is arranged at a distance from the privacy beacon that is below a threshold distance, no status signal is transmitted by the mobile module to the central unit.

The range-finding unit is preferably configured to estimate a distance between the mobile module and at least one beacon as a function of the strength or the power of the transmission signal sent by the beacon to the mobile module.

The range-finding unit is preferably configured to estimate several distances between the mobile module and respectively a plurality of beacons as a function of transmission signals respectively transmitted by each beacon to the mobile module. The processing unit then can be configured such that the position signal corresponds to a position of the mobile module relative to several beacons. According to one possibility, the position signal is or comprises a list of estimated distances between the mobile module and each beacon.

According to one embodiment, the processing unit is configured for:

estimating a status of the user, from among a plurality of predetermined statuses, from at least one activity signal established by the activity sensor; and generating the status signal as a function of the estimated status of the user.

The status of the user can represent a physical activity undertaken by the user at the measurement time, or a stress status of the user at the measurement time, or a physiological status of the user at the measurement time.

According to one embodiment, the status signal corresponds to the activity signal, optionally pre-processed, resulting from the activity sensor or each activity sensor. The status signal can be acquired by associating or by combining the activity signal resulting from various activity sensors. The status signal can be equivalent to the activity signal.

The short-range connection notably can be a connection with a range of less than 50 meters or 30 meters.

According to one embodiment:

at least one beacon comprises an ambience sensor, configured to measure a temperature and/or a sound level and/or a light level;

the beacon is configured to transmit an ambience signal to the mobile module that is dependent on the measurement carried out by the ambience sensor; and the processing unit is programmed to assign an ambience level to each status signal that is dependent on the ambience signal.

According to this embodiment, the central unit gathers the position signal, the status signal and the ambience level at each measurement time.

A second aim of embodiments of the disclosure is a method for monitoring a status of a user of a device according to the first aim of embodiments of the disclosure, with the user being placed in an environment, with the user wearing the mobile module of the device, with several beacons of the device being distributed in the environment, the method comprising, for at least one measurement time:

a) measuring an activity of the user, using an activity sensor of the mobile module;

b) generating a status signal from the activity measured by one or each activity sensor;

c) estimating a distance between the mobile module and at east one beacon;

d) determining, from the distance or from each distance resulting from c), a position signal representing a position of the user in the environment; and e) transmitting the status signal and the position signal of the user, determined at each measurement time, to a central unit.

The central unit is different from the mobile module.

At least one beacon can be fixed in the environment. Preferably, several beacons are fixedly distributed in the environment.

According to one possibility, a beacon can be worn by a third party, other than the user.

According to one possibility:

the environment comprises an object, likely to be in contact with the user or handled by the user; and at least one beacon is attached to the object.

According to one possibility, at least one beacon is a privacy beacon, with the device being programmed such that when the mobile module communicating with the privacy beacon is arranged at a distance from the privacy beacon that is below a threshold distance, no status signal is transmitted by the mobile module to the central unit.

According to one possibility:

at least one beacon comprises an ambience sensor, configured to measure a temperature and/or a sound level and/or a light level;

the beacon is configured to transmit an ambience signal to the mobile module that is dependent on the measurement carried out by the ambience sensor; and the processing unit is programmed to assign an ambience level to the status signal transmitted to the central unit that is dependent on the ambience signal.

The central unit can be present in the environment or remote from the environment.

The environment is preferably a place intended to be inhabited by the user. It can be a workplace. The environment preferably corresponds to all or part of a residential building or a building intended for work activity.

Further features of the first and second aim of embodiments of the disclosure can be found in the accompanying claims.

A third aim of embodiments of the disclosure is a measurement system, comprising:

several devices according to the first aim of embodiments of the disclosure, with the devices being intended to be respectively worn by various users; and a central unit, configured to receive the status signal and the established position signal respectively, at each measurement time, for the various users;

with the central unit being programmed for:

taking into account a predetermined task;

selecting, from the status and position signals transmitted to the central unit, for each user, measurement times during which each user undertakes the task, with the measurement times selected for each user forming at least one time range specific to each user; and processing, for each user, the status signals and/or the position signals in each selected time range for the user, so as to characterize the activity of each user when the user completes the predetermined task.

According to this embodiment, preferably, only the signals transmitted to the central unit during the time range specific to each user are used to characterize the activity of the user for the task that is taken into account.

The third aspect (or aim) of embodiments of the disclosure can be implemented simultaneously by respectively considering various tasks that are carried out by each user.

Embodiments of the disclosure will be better understood upon reading the description of the embodiments that are presented, throughout the remainder of the description, with reference to the figures listed below.

BRIEF DESCRIPTION OF THE DRAWINGS

In FIG. 2A, the abscissa axis corresponds to the time (unit: millisecond (ms)) and the ordinate axis corresponds to the acceleration (unit: mg or milli-g).

In FIG. 2B, the abscissa axis corresponds to the time (unit: millisecond (ms)) and the ordinate axis corresponds to the acceleration (unit: mg or milli-g).

FIG. 9A corresponds to an average walking period, without contextualization, with the test user moving in two different rooms.

FIG. 9B corresponds to a duration for standing up from a chair, without contextualization, with the user using two different chairs.

FIG. 9C corresponds to an average walking period, the measurements being contextualized, the test user moving in the same room.

FIG. 9D corresponds to an average walking period, the measurements being contextualized, the test user moving in the same room, different from the room corresponding to FIG. 9C.

FIG. 9E corresponds to a duration for standing up from a chair, the measurements being contextualized, the test user using the same chair.

FIG. 9F corresponds to a duration for standing up from a chair, the measurements being contextualized, the test user using the same chair, different from the chair corresponding to FIG. 9E.

DETAILED DESCRIPTION

Figures 1A, 1B:
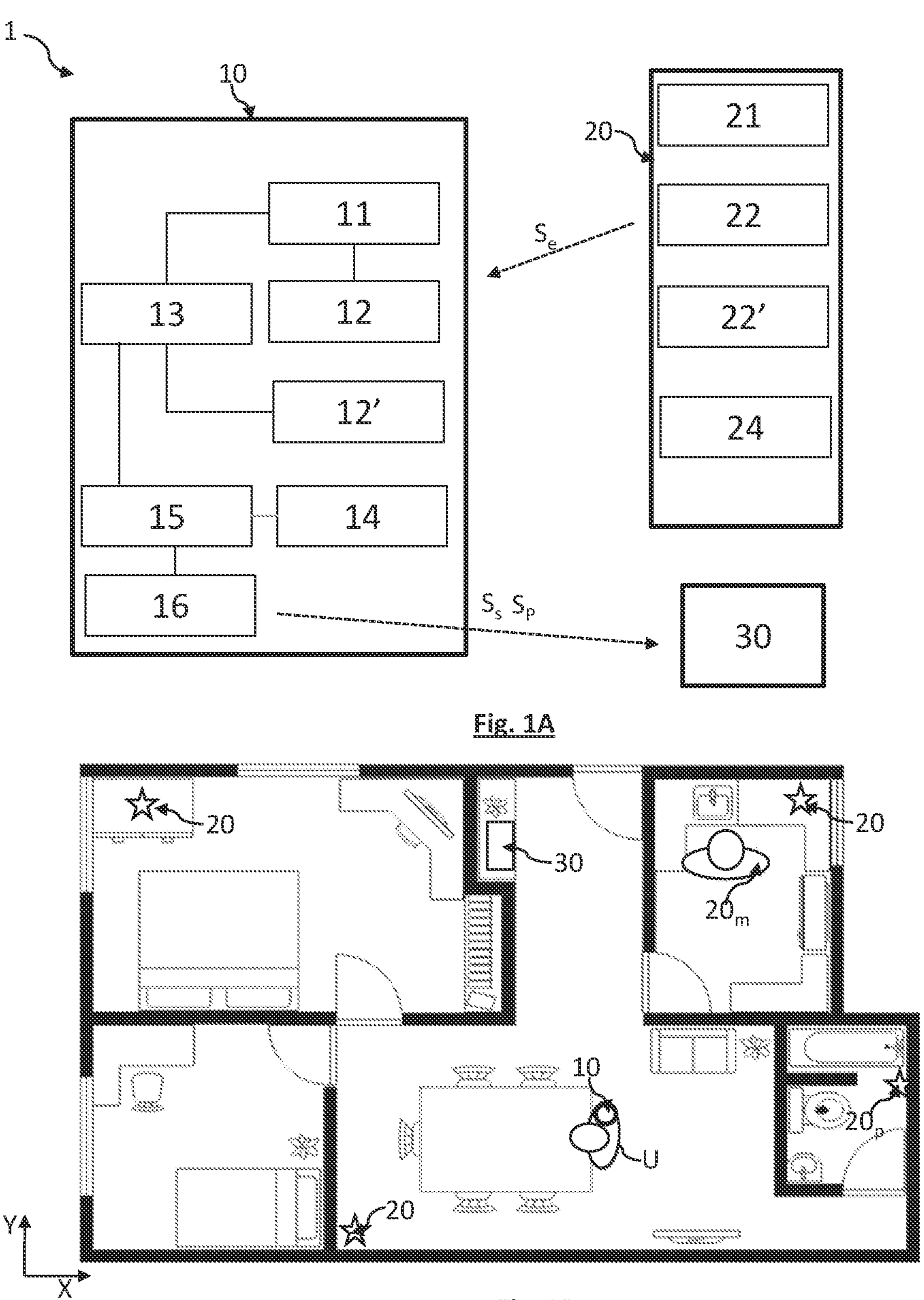
FIG. 1A schematically shows the main components of a device according to embodiments of the disclosure.
FIG. 1B shows an example of the distribution of beacons in an environment, with the environment being a residence.

FIG. 1A schematically shows the three main components of a device according to embodiments of the disclosure. The device 1 comprises a mobile module 10, intended to be worn by a user. The mobile module can be arranged, for example, in contact with the body of the user, being held by a bracelet or an armband, for example. The mobile module 10 can be integrated into a watch.

The mobile module 10 is intended to communicate, via a short-range wireless connection, with a beacon 20, and preferably with several beacons 20. A short-range connection is understood to mean a connection that is established, generally by radio waves, within a range of a few tens of meters: without obstacles, the range is less than 50 meters or even 30 meters. It can involve, for example, an ultra-high frequency (UHF) radio wave communication, for example, of the Bluetooth type, or, preferably, a Bluetooth Low Energy (BLE) communication. Such a protocol is the subject of a standard published by Bluetooth SIG (Bluetooth Special Interest Group). Alternatively, the connection can be of the ZigBee type, which, like the Bluetooth or Bluetooth Low Energy connection, uses radio waves at a frequency of 2.4 GHz.

The mobile module 10 comprises a wireless connection unit 11, intended to communicate, via the short-range wireless connection, with beacons 20 located within range of the mobile module. The wireless connection unit 11 is connected to an antenna 12 exhibiting a reception pattern. In a known manner, the reception pattern corresponds to an angular variation of the sensitivity of the reception of the antenna. Generally, the reception pattern of an antenna is not isotropic.

The device comprises at least one beacon 20, and preferably several beacons 20, distributed in an environment. The environment is a space, generally covered, that the user is likely to occupy. It can involve, for example, a residence, or a workplace, or a shared residence, for example, a rest home or an establishment for accommodating elderly people. The environment can include outdoor spaces, for example, a garden. However, a targeted use of embodiments of the disclosure relates to the inside of a building, in which GPS (Global Positioning System) positioning can be affected by malfunctions or cannot be fully operational.

Each beacon 20 comprises a transmission unit 21, intended to transmit a transmission signal $S_e$ to the mobile module 10, according to the short-duration wireless connection on the basis of which the mobile module 10 communicates. The transmission unit 21 is connected to an antenna 22, which is intended to transmit or receive a signal. Like the antenna 12 equipping the mobile module, the antenna 22 of each beacon 20 is characterized by a transmission/reception pattern, which generally is non-isotropic.

The mobile module can advantageously comprise an orientation unit 12', intended to estimate an orientation of the mobile module, and more specifically an orientation of the antenna 12. The orientation unit 12' can implement an accelerometer, in order to estimate the orientation of the antenna. Advantageously, the orientation unit 12' comprises a magnetometer combined with the accelerometer. The accelerometer can belong to an activity sensor 14 described below. The orientation of the antenna can be used by the range-finding unit 13 so as to improve the estimation of the distance. Indeed, with the reception sensitivity of the antenna 12 varying angularly, the orientation of the antenna can be used to take into account a variation in sensitivity in the estimation of the distance.

The mobile module 10 also comprises a range-finding unit 13, configured to estimate, at different measurement times, a distance between the mobile module 10 and at least one beacon 20, or even each beacon 20 located within the range of the mobile module 10. Each distance between the mobile module 10 and a beacon 20 is estimated on the basis of a measurement of the power of the transmission signal transmitted by the beacon 20 and received by the mobile module. It is known that the power of the signal received by a radio wave receiver allows the distance to be estimated between the radio wave transmitter (in this case the beacon 20) and the radio wave receiver (in this case the mobile module 10), according to the following expression:

$$d = 10^{\frac{(P - RSSI)}{10 \times N}} \qquad \text{Expression (1)}$$

where:

- d is the estimate of the distance between the beacon 20 and the mobile module 10;
- P is the power of the signal transmitted by the beacon (dB);
- N is a constant, usually ranging between 2 and 4, the value of which can be adjusted by the orientation unit 12'; and
- RSSI ("Received Signal Strength Indicator"), corresponds to the power of the signal transmitted by the antenna and received by the mobile module (dB).

The mobile module 10 comprises at least one activity sensor 14. The activity sensor 14, or each activity sensor 14, is configured to measure an activity of the user and to transmit an activity signal $S_a$ representing the activity of the user. The activity sensor can be selected from among:

- a motion sensor, for example, of the gyrometer or accelerometer or magnetometer type;
- a cardiac activity sensor, for example, a sensor operating according to the photoplethysmography principle, a technique that is usually used on sports watches;
- a muscle activity sensor, for example, an electromyography sensor;
- a brain activity sensor, for example, an electroencephalography (EEG) type sensor;
- a blood pressure sensor, for example, a sensor based on a pulse wave velocity;
- an electrodermal activity sensor, configured to measure an impedance of the skin, in particular in the event of a stressful situation;
- a temperature sensor;
- an atmospheric pressure sensor; and
- an analyte sensor, for example, a glucose sensor, with the concentration of some molecules being able to be detected by a photoacoustic method or by analyzing a body fluid, for example, sweat. It also can be a biochemical sensor.

The activity sensor or each activity sensor 14 is preferably non-invasive and non-intrusive in the body of the user. Each activity sensor 14 can particularly implement an optical or acoustic or electrical or electrochemical method.

The atmospheric pressure sensor can allow particular tasks that are carried out by the user to be identified, for example, ascending or descending a staircase. This takes advantage of the detection of a variation in the atmospheric pressure measured by the sensor in order to determine a variation in the altitude of the user.

The term "activity" can correspond to a physical activity of the user, or to a physiological activity of the user: it can be a cardiac activity, a muscular activity, a neurological activity. It also can be a psychiatric activity, for example, the occurrence of a stressful situation for the user, or the occurrence of a state of drowsiness. It also can be an activity representing a status that is considered to be pathological: for example, the appearance of tremors or an akinesia in a user affected by Parkinson's disease.

The activity signal transmitted by each activity sensor 14 can be one-dimensional or multi-dimensional. When the activity sensor is an accelerometer or a gyrometer or a magnetometer, the activity signal is usually three-dimensional.

The mobile module 10 also comprises a processing unit 15, configured to process the activity signal established by the activity sensor or each activity sensor 14 so as to establish a status signal $S_s$ of the user. According to one possibility, the processing unit can carry out simple signal processing operations, for example, amplification and/or shaping and/or digitization. The status signal $S_s$ then corresponds to the activity signal $S_a$, or to each activity signal, resulting from the processing. According to another possibility, the processing unit 15 can be programmed to interpret the activity signal $S_a$, or each activity signal, so as to estimate a status of the user from among several predetermined statuses. The status signal $S_s$ then corresponds to the estimated status of the user. The status of the user can be selected from among:

- an active status (user performing regular movements) or rest state, similar to sleeping;
- a type of movement performed by the user: walking, transitioning from the sitting position to the standing position, transitioning from the standing position to the sitting position, transitioning from the lying position to the standing position, transitioning from the standing position to the lying position, tremors, walking up a staircase, turning over, running, jumping, falling;
- a symptomatic status: tremors, agitation, disordered movements; and
- a stressful status.

The status signal $S_s$ also can be or can comprise a feature of a movement of the user, for example, an average time period between two consecutive steps, or a movement speed, or a speed for completing a particular movement. It can involve, for example, a temporal or frequency feature.

The status signal $S_s$ is generated by the processing unit 15, from one or more activity signals $S_a$ respectively resulting from one or more activity sensors 14. The processing unit 15 can implement a classification algorithm. The classification algorithm can be a monitored artificial intelligence algorithm, having been trained, for example, by a decision tree-type algorithm.

The processing unit 15 can be made up of analogue or digital circuits. It can comprise a microprocessor, particularly when implementing the classification algorithm described above.

The processing unit 15 can also estimate a position of the user from the distance between the mobile module and each beacon. The term "position" is understood to mean a position of the user in the environment in which the beacons 20 are distributed. For example, it can be a room occupied by the user.

The mobile module 10 also comprises a transmission unit 16. The transmission unit 16 is configured to transmit the status signal, resulting from the processing unit 15, to a central unit 30 described hereafter.

In addition to a transmission unit 21 connected to an antenna 22, each beacon 20 can advantageously comprise an orientation unit 22', intended to establish an orientation of the antenna 22 of the beacon 20. In this case, it involves taking into account an angular variability of the transmission power of the antenna 22 when the range-finding unit 13 of the mobile module estimates the distance.

Each beacon 20 can also comprise an ambience sensor 24, intended to measure information relating to an ambience parameter, at the position occupied by the beacon. The ambience parameter can be selected from among: the temperature and/or a sound level and/or a brightness. Depending on the ambience parameter that is used, the ambience sensor 24 can be a thermometer, or a microphone or a photodetector.

The mobile module 10 is configured to be connected to a central unit 30. The central unit 30 is intended to receive signals transmitted by the mobile module 10. This particularly involves status signals and information relating to the position of the user at various measurement times. The central unit 30 comprises a memory, for storing the signals received over time by the mobile module or by various mobile modules that are simultaneously used.

The central unit 30 can comprise a microprocessor for analyzing the stored signals. When the status signal $S_s$ is formed by each activity signal $S_a$, optionally pre-processed, the status of the user can be classified in the central unit 30 on the basis of the status signal transmitted by the mobile module 10.

The transmission of signals between the mobile module 10 and the central unit 30 is preferably carried out by a long-range wireless connection, for example, Wi-Fi, or by a mobile telephone network, for example, of the 3G, 4G or 5G type.

FIG. 1B shows an example of the distribution of beacons 20 in an environment that corresponds to a residence occupied by a user U. The environment has been schematically shown in the form of a horizontal plane. Beacons 20 are distributed in various rooms that are intended to be occupied by the user: bedroom, lounge, kitchen, toilets. The central unit 30 is arranged in the entrance. In other configurations, the central unit 30 is remotely located, for example, in a data storage and analysis center, gathering the status signals transmitted by the mobile modules of various users. The beacons 20 are generally attached to particular rooms, or to particular objects. For example, a beacon can be fixed on a chair or on a table, or on a particular household appliance. Preferably, some beacons are fixedly arranged in the environment.

In FIG. 1B, the user U is seated and wearing the mobile module 10. A mobile beacon $\mathbf{20}_m$, worn by a third party, is shown in the kitchen. This is a mobile beacon, attached to an individual other than the user: medical personnel or a family member. In the case of collective housing, the third party can be another occupant of the collective housing.

FIG. 1B also shows a privacy beacon $\mathbf{20}_p$ located in the bathroom. When the mobile module is arranged in the vicinity of the privacy beacon $\mathbf{20}_p$ then sending data to the central unit 30 is interrupted. The use of a privacy beacon ensures that the privacy of the user is preserved in certain areas, called "private" areas, of the residence, in which the user does not want their status to be determined and analyzed. A privacy beacon $\mathbf{20}_p$ can be arranged in the toilet, in a bathroom or in a bedroom. The use of a privacy beacon $\mathbf{20}_p$ is an important element in order for the device 1 to be accepted by the user.

An important aspect of the device is the ability to measure data, representing daily activity of the user, in a closed or partly closed environment, while assigning these data with a position signal $S_p$, representing a position of the user in the environment. Indeed, it was considered, for the embodiments disclosed herein, that the activity of the user can vary as a function of their position in a given environment. The association between signals, representing the activity of the user, expressing their status, and the location of the user in the environment, allows data to be acquired that is acquired in a particular context. This is referred to as contextualized data. The data, when they are contextualized, i.e., associated with a position of the user, exhibit less dispersion, and are easier to analyze.

Figure 2A:
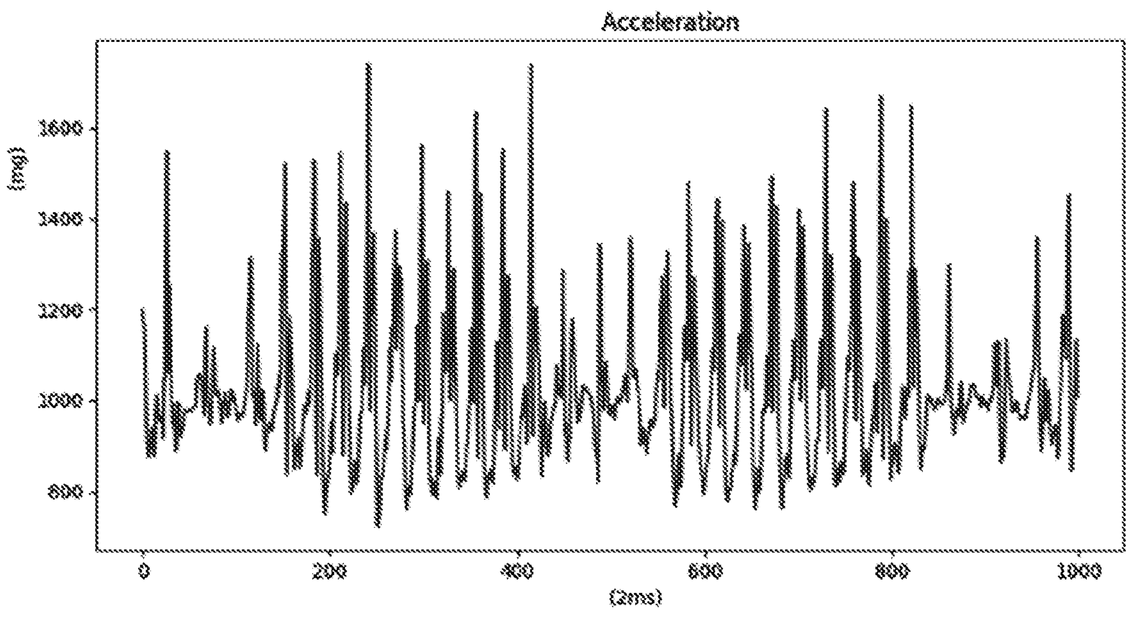
FIG. 2A shows an activity signal produced by an accelerometer when the user moves into a large room.
Figure 2B:
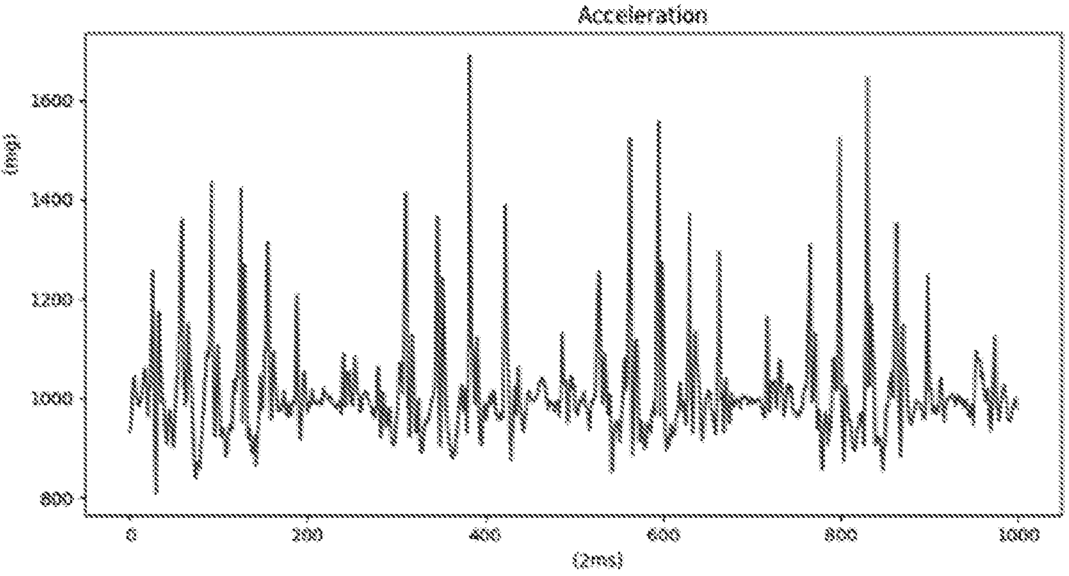
FIG. 2B shows an activity signal produced by an accelerometer when the user moves into a small room.

FIGS. 2A and 2B show an acceleration signal, measured by an accelerometer worn by a user respectively moving in a large room and in a small room. The abscissa axis corresponds to the time (unit ms) and the ordinate axis corresponds to the normal of the acceleration. It can be seen that, although they originate from the same sensor, the signals measured by the accelerometer do not have the same features. Thus, the average periods of the steps of the user in the large room and in the small room are 587 milliseconds and 658 milliseconds, respectively. Thus, the average time period of the steps can form a status signal, characterizing the activity of the user. This example shows that the status signal varies as a function of the position of the user, and, more specifically, as a function of the room occupied by the user.

In order to achieve a more accurate analysis of the activity of the user, it is understood that it is preferable to dissociate the signals grouped as a function of the position of the user, in this case the room occupied by the user. Thus, associating an item of information relating to the position of the user allows the variability of information relevant to monitoring the user to be reduced.

Figure 3:
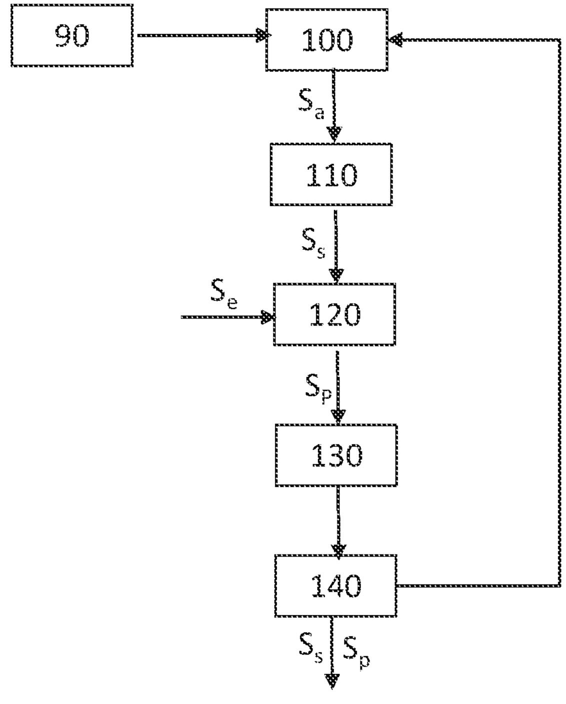
FIG. 3 schematically shows the main steps of a method for implementing the device shown in FIG. 1A.

FIG. 3A schematically shows the main steps of a method for implementing the device 1 described above. The implementation of the method assumes that the position of the beacons 20 is known: each beacon is thus assigned to a room, or to an object, or to an individual. Each beacon is assigned an identifier that is specific thereto. Two different beacons have two different identifiers. It is preferable for several beacons to be fixed in the environment.

Step 100: Acquiring Activity Signals

During this step, each activity sensor 14 of the mobile module 10 generates an activity signal $S_a$ at a measurement time. It can be an accelerometer signal and a heart rate signal, for example.

Step 110: Generating a Status Signal

Based on the activity signal $S_a$ generated by each activity sensor 14, the processing unit 15 establishes a status signal $S_s$ of the user. In general, the status signal $S_s$ characterizes the activity of the user.

According to a first possibility, the status signal $S_s$ corresponds to a set formed by each activity signal $S_a$ transmitted by each activity sensor 14, optionally after applying processing of the filtering, shaping, amplification, digitization type. The processing unit 15 can be configured to extract features of each activity signal $S_a$, for example, average, variance, or other statistical indicators, peak detection, peak-to-peak distance, minimum, maximum, a dominant frequency, a time period of a movement performed by the user. The status signal $S_s$ can comprise features extracted from each activity signal $S_a$. According to this possibility, the status signal $S_s$ gathers the activity signals $S_a$ measured by each activity sensor 14, and/or the features of the activity signals $S_a$ measured by each activity sensor.

According to a second possibility, the processing unit 15 is programmed to implement a classification algorithm, so as to estimate a status of the user, from among several predetermined statuses, as described above. The classification algorithm can be based on features extracted from each activity signal. In this case, the status signal $S_s$ represents the status of the user.

Step 120: Measuring Distances Between the Mobile Module and at Least One Beacon, and Preferably Each Beacon Located Within the Range of the Mobile Module During this step, the range-finding unit 13 of the mobile module 10 estimates a distance between the module and each beacon 20 arranged within the range of the short-duration connection of the wireless connection unit 11. As mentioned above, the distance is estimated on the basis of the strength of a transmission signal $S_e$ transmitted by the beacon and picked up by the mobile module. In order to refine the measurement of the distance, the respective orientations of the antennas 22, 12 of the beacon and of the mobile module, relative to the vertical, can be taken into account, using an accelerometer present in the beacon and in the mobile module 10. This enables a comparison of the transmission/reception patterns, so as to take into account variations in the transmission power (on the beacon) and in the reception sensitivity (on the mobile module 10).

When several beacons 20 are within range of the mobile module 10, the transmission signal $S_e$ sent by each beacon comprises the identifier of the beacon, so as to acquire a list of distances between the mobile module 10 and each beacon 20. The identifier also allows the type of beacon to be identified: fixed beacon, beacon attached to an object, beacon worn by an individual, or privacy beacon.

According to a first possibility, each beacon 20 transmits a transmission signal $S_e$, comprising its identifier, at a regular frequency. In this case, the mobile module periodically receives the transmission signal $S_e$, and the range-finding unit 13 determines the distance between the beacon and the mobile module on the basis of the transmission signal $S_e$.

According to another possibility, when an activity sensor 14 detects a significant variation in an activity signal, the wireless connection unit 11 of the mobile module 10 transmits a connection signal to each beacon. Each beacon that has detected the connection signal generated by the mobile module transmits a transmission signal $S_e$, which is detected by the antenna 12 of the mobile module and is transmitted to the range-finding unit 13. This possibility is considered to be less energy consuming by the mobile module, and more energy consuming for the beacon. This possibility is preferred since the mobile module must be as compact as possible. The beacons do not need to be as compact.

Figure 4A:
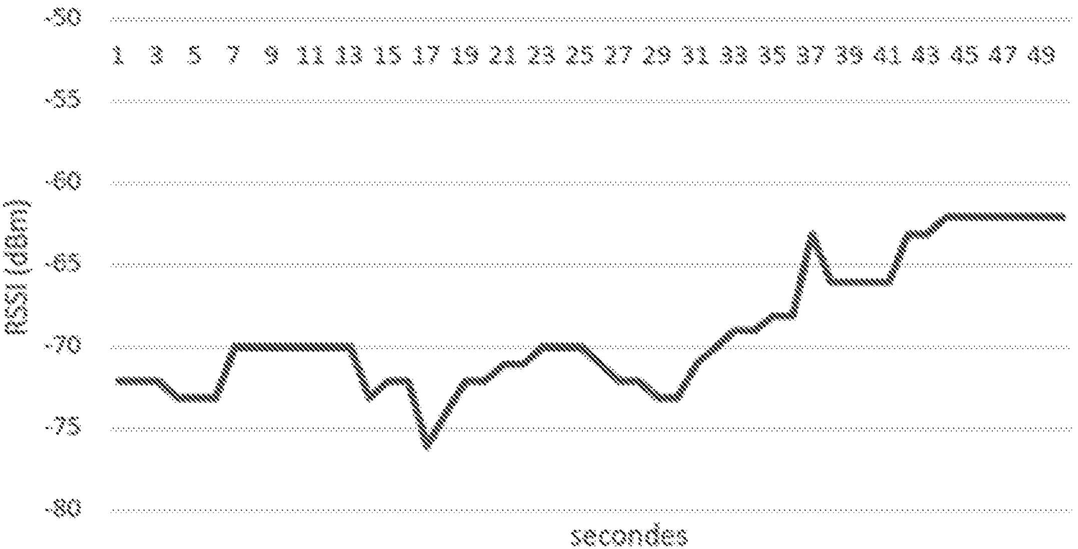
FIG. 4A shows the power of a signal transmitted by a beacon and received by a mobile module. The abscissa axis corresponds to the time (unit: seconds) and the ordinate axis corresponds to the power received by the mobile module (unit: dBm).
Figure 4B:
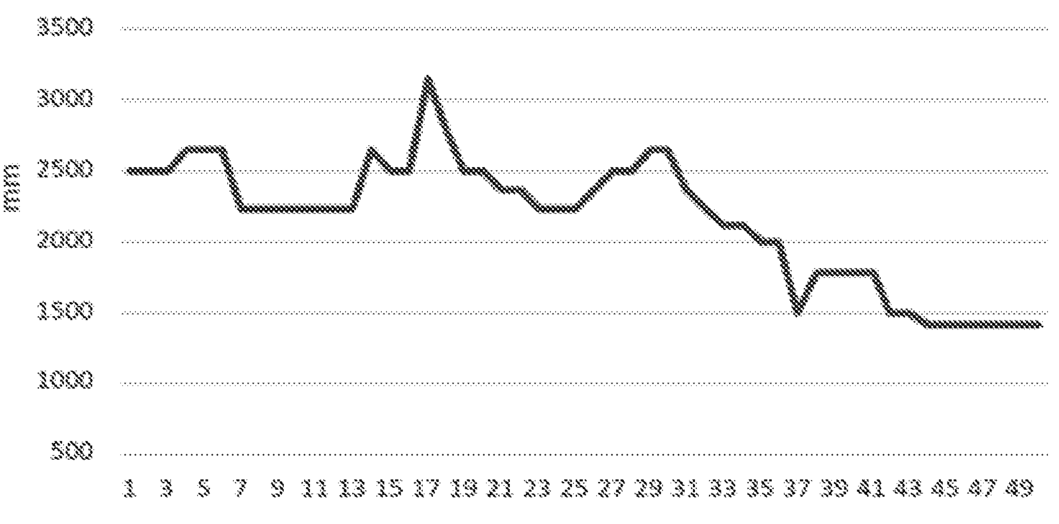
FIG. 4B shows an estimate of a distance between the mobile module and the beacon, with the distance being computed as a function of the signal shown in FIG. 4A. The abscissa axis corresponds to the time (unit: seconds) and the ordinate axis corresponds to an estimated distance (unit: mm).

FIGS. 4A and 4B respectively show a temporal evolution of the RSSI power of a transmission signal $S_e$ transmitted by a beacon 20 and detected by a mobile module 10, as well as the distance estimated from the power, according to the expression (1). In FIGS. 4A and 4B, the abscissa axis corresponds to the time (seconds) and the ordinate axis corresponds to the RSSI (unit: dBm) and to the distance (unit: mm). Dbm is a power in decibels relative to a reference value of 1 milliwatt (mW).

Most of the beacons 20 are fixed and therefore can be connected to large capacity batteries or directly to the electrical network. The embodiments by which the power consumption of the mobile module is minimized, to the detriment of the beacons, will be preferred.

According to one possibility, the transmission signal $S_e$ transmitted by the beacon 20 comprises a component representing the level of an ambience parameter measured by the ambience sensor 24: as previously indicated, it can be a temperature value, a brightness value or an ambient sound level value: the value of the ambience parameter is transmitted to the processing unit 15 of the mobile module. Indeed, the activity of the user can be sensitive to such an ambience parameter.

As mentioned with reference to FIG. 1B, a beacon $\mathbf{20}_m$ can be worn by a third party individual likely to interact with the user. The measurement of the distance between the worn beacon $\mathbf{20}_m$ and the mobile module 10 constitutes an indication that the user interacts with the individual wearing the beacon. Their behavior is likely to be influenced by the presence of the individual. Thus, the proximity of a third party is a relevant datum, which can be considered to be an ambience parameter, in the same way as the temperature or the brightness or the sound level, and can allow contextualization of the activity measurements and the status signal $S_s$ of the user generated by the processing unit 15.

Step 130: Determining a Position of the User

During step 130, the processing unit 15 determines a position of the user in the considered environment, as a function of the distance, or, and preferably, as a function of several distances respectively measured between the mobile module 10 and each beacon 20 considered to be immobile in the environment. The position of the beacons 20 is then stored in the processing unit 15. Determining the position of the user results from a comparison between the measured distances and the position of each beacon, with the exception of a possible worn beacon $\mathbf{20}_m$. The position of the user can be determined by implementing a triangulation algorithm. Thus, the position of the user is preferably determined relative to various beacons 20, which beacons are considered to be fixed in the environment of the user.

When a beacon is attached to an immobile object, or which can be considered as such, a single measured distance al lows the position of the user to be estimated. Thus, when the user is sitting on a chair on which a beacon is fixed, the position of the user can be determined when the distance between the beacon, which is fixed on the chair, and the mobile module is below a certain threshold.

The position of the user, resulting from step 130, can be such that the user is located within a defined privacy perimeter, in which storing and analyzing the activity or the status of the user by the central unit 30 is not desirable. This corresponds, for example, to the bathroom, shown in FIG. 1B, or to a bedroom. The presence of the user within the privacy perimeter is detected when the distance between the privacy beacon $\mathbf{20}_p$ is below a predetermined threshold value. The position of the user within the privacy perimeter can be confirmed by other distances between other beacons, in particular fixed beacons, by implementing a triangulation algorithm, for example.

According to an alternative embodiment, the position of the user is estimated on the central unit 30. In this case, the position signal, which is transmitted with the status signal $S_s$, can comprise a list of estimated distances between the mobile module and a beacon, preferably a plurality of beacons, notably fixed in the environment of the user.

On completion of step 130, a position signal $S_p$ is available that represents the position of the user in the environment. This is either an estimated position, for example, a room in which the user is located, or a distance or a list of distances allowing the position to be estimated.

Step 140

During step 140, the transmission unit transmits the status signal $S_s$ and the position signal $S_p$ of the user at each measurement time to the central unit 30. Optional ambience parameters can be assigned to the status signal $S_s$, such as the temperature, the brightness, the ambient sound level, or the presence of a third party wearing a worn beacon $\mathbf{20}_m$ The status signal $S_s$ is thus contextualized, in the sense that it represents not only the activity of the user, but also conditions in which this activity is undertaken: position and/or ambience level.

According to one possibility, the position and status signals are stored in a memory of the mobile module 10 and sequentially transmitted to the central unit 30, for example, according to a determined frequency.

Steps 100 to 140 are repeated, with each iteration allowing a status signal $S_s$ and a position signal $S_p$ of the user, and optionally a value of an ambience parameter (presence of an individual, temperature, etc.) to be acquired at a measurement time. Steps 100 to 140 can be repeated continuously, or as long as the mobile module 10 is considered to be active. To this end, the mobile module 10 can execute a step 90, allowing the mobile module 10 to transition between a standby state and an active state.

In order to minimize the power consumption of the mobile module 10, the module can enter a standby mode when no activity, or no significant variation in activity, is detected by an activity sensor 14. When a variation in activity is detected, the processing unit 15 can "wake up" the main components of the mobile module, so as to activate the wireless communication with the beacons and carry out the distance computations. The processing unit 15 can implement an algorithm, for example, an artificial intelligence algorithm with supervised learning, to transition the mobile module from the standby state to the active state, on the basis of signals originating from activity sensors 14, and in particular from signals representing a motor activity of the user.

The data transmitted to the central unit 30 are intended for monitoring the user. This can involve monitoring a convalescence, or monitoring the evolution of a state of health. When the transmitted data represent an abnormal situation, the central unit 30 can detect an occurrence of an emergency situation and transmit a warning signal. An abnormal situation can be excessive shaking, an extended immobile position in one position, in the environment occupied by the user, and not intended for rest, a sudden acceleration to a position corresponding to a staircase, that may indicate a fall, or an increase in the heart rate while the user is located in a position corresponding to a rest location, for example, an armchair or a bed. A warning situation can correspond to a lack of distance measurement, with the fixed beacons located in the residence being outside the range of the mobile module, potentially indicating that the user has ventured outside their residence.

Experimental Tests

FIGS. 5A to 5E show an example of data resulting from tests, during which two test users have been asked to perform motor skills tasks. The test users wore a mobile module, as described above, on a belt. The users are placed in a test environment made up of two rooms. A first room was small. A second room was larger. The test users are placed in the environment. The mobile module of each test user allowed the room occupied by the user to be located, so as to separate the measured data as a function of the room occupied by each user.

The users wore a mobile module comprising an STM32L433 microcontroller (ST Microelectronics), connected to a Fanstel BLE BC832 connection unit, as well as to an LSM6DSOX inertial unit (ST Microelectronics). This type of inertial unit has a circuit for executing an algorithm for interpreting the measured activity signals. In this application, the circuit of the inertial unit was programmed to estimate the period of a walking cycle, usually referred to as "Step Time." Thus, in this example, the status signal $S_s$ was the duration of the walking cycle.

FIGS. 5A to 5E show walking cycle times (ordinate axis—unit: ms) determined for each test user (abscissa axis), with this respectively being in the large room, the large room with three obstacles, the small room, the small room with two obstacles, as well as in all the configurations. FIGS. 5A to 5D represent contextualized status signals, i.e., assigned to a position of the user (large room, large room with obstacles, small room, small room with obstacles), while FIG. 5E corresponds to non-contextualized data, i.e., without taking into account the position of the user.

Figures 5A, 5B, 5C, 5D, 5E:
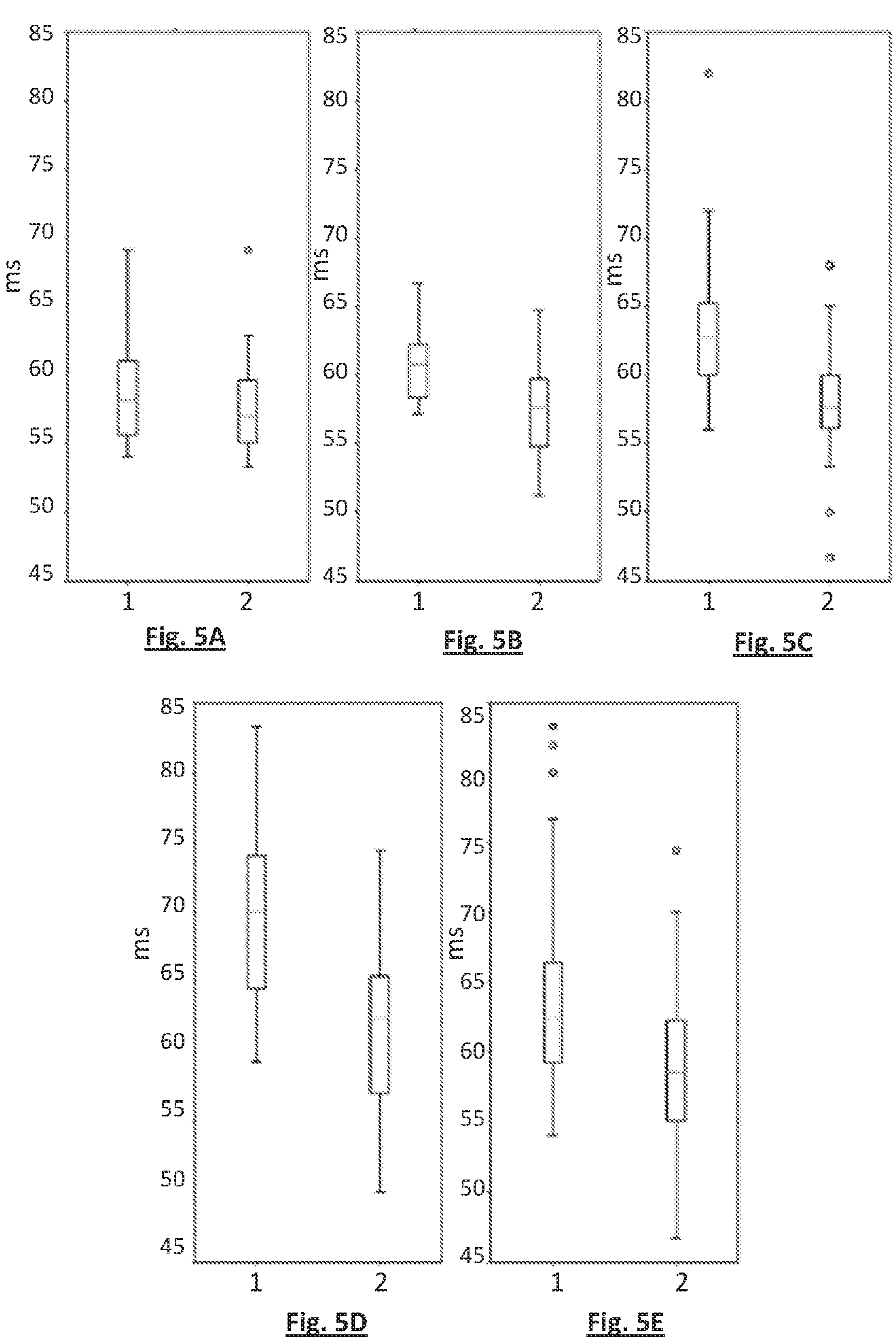
FIG. 5A, FIG. 5B, FIG. 5C, FIG. 5D, and FIG. 5E are box plots showing the variability of an average walking cycle period (usually referred to as step time), measured by mobile modules respectively worn by two test users: user 1 and user 2. The abscissa axis designates the user and the ordinate axis corresponds to a time unit (ms).

In each figure, the status signals have been shown in the form of a box plot, indicating the median, the quartiles and the extrema. Each extremum respectively corresponds to the first quartile decreased by 1.5 times the interquartile deviation, as well as to the third quartile increased by 1.5 times the interquartile deviation. It can be seen that the contextualized data (FIGS. 5A to 5D) are less dispersed than the non-contextualized data (FIG. 5E). Thus, an important aspect of embodiments of the disclosure is to be able to transmit signals, representing the user, but also the context in which the signals have been acquired, in particular the position and optionally other ambience factors. This allows the variability of the data to be significantly reduced: the characterization of the user is then more accurate. Furthermore, it can be seen that the median value of the walking cycle varies as a function of the room in which the user is moving: the smaller and/or the more cluttered the room, the more the duration of the walking cycle increases.

In the present case, by analyzing the contextualized data, by connecting them to the room in which the user is moving, it is easier to detect a change in the symptoms of the user, with a worsening of the symptoms possibly resulting in a reduction in the walking cycle. A variation can be more easily detected when the variability of the measurements is low.

Embodiments of the disclosure allow precise analysis of the evolution of the symptoms of a patient in situ, i.e., in their place of residence. Test sessions that are performed in a hospital environment and in a standardized environment are thus avoided, which corresponds to the current practice for patients with Parkinson's disease. By implementing embodiments of the disclosure, the patient can be monitored on the basis of motor skills data acquired at their home and can be contextualized, i.e., grouped as a function of the position of the user. In this example, the position of the user corresponds to the room occupied by the user.

Figures 6A, 6B, 6C:
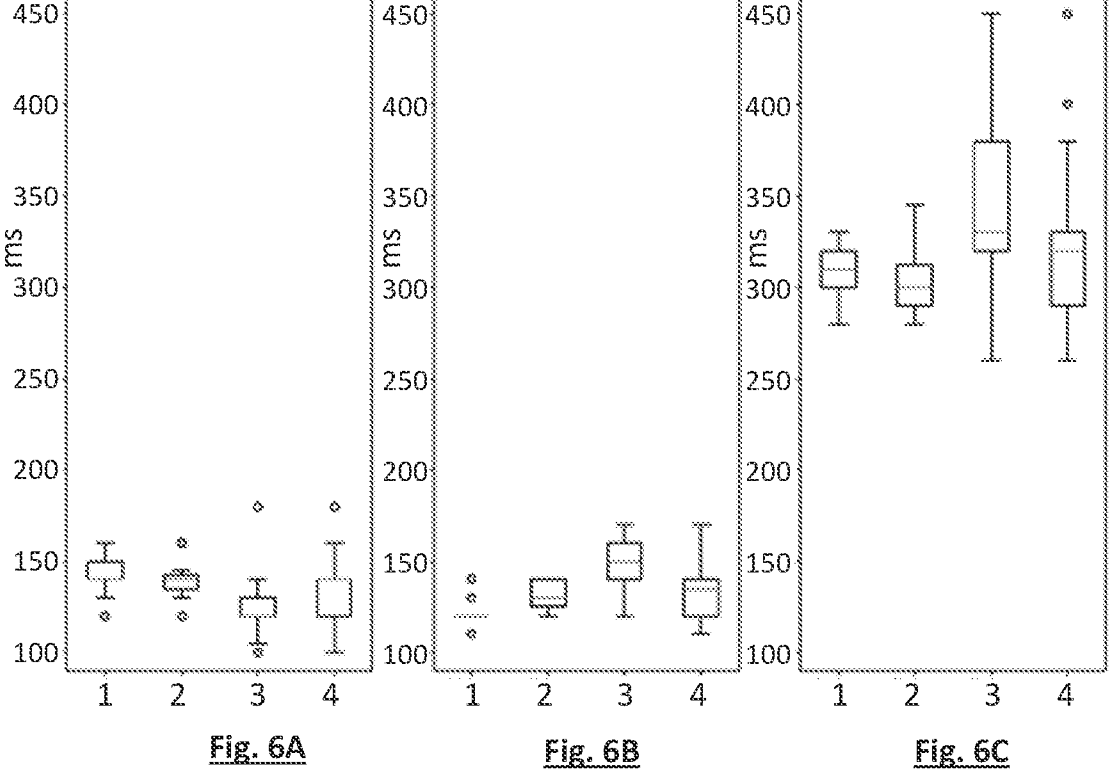
FIG. 6A, FIG. 6B, and FIG. 6C are also box plots representing a variability of a duration for sitting on a chair, or "sit time" (FIG. 6A), a duration for standing up from a chair, or "stand time" (FIG. 6B), or a duration for sitting and standing up, or "sit to stand time" (FIG. 6C). In each figure, the abscissa axis designates the type of chair. 1: chair height 39.5 cm; —2: chair height 51.5 cm; —3: chair height 59.5 cm; —4: all chairs combined. On each ordinate axis, the unit is a millisecond.

FIGS. 6A to 6C illustrate another example of use, in which a test user was asked to sit and to stand on different chairs, with different heights. FIGS. 6A to 6C respectively show the durations for sitting, and standing up and the durations of a sitting-standing cycle, with this type of duration usually being referred to as "sit to stand time". In each figure, the ordinate axis corresponds to the computed duration and the abscissa axis corresponds to the height of the chair (unit: ms). In each figure, the abscissa axis designates the type of chair. 1: chair height 39.5 cm; —2: chair height 51.5 cm; —3: chair height 59.5 cm; —4: all chairs combined (no contextualization). The data are shown in the form of box plots, as described with reference to FIGS. 5A to 5E. It can be seen that, depending on the type of chair, the median value varies, as does the variability. The contextualization of the data, namely the position of the user on a chair of known height, allows the analysis to be more accurate. This example can be implemented by arranging different beacons on different chairs. The position of the user relative to a chair is determined by a simple distance measurement. The occupied chair corresponds to the beacon closest to the user.

Figures 7A, 7B, 7C:
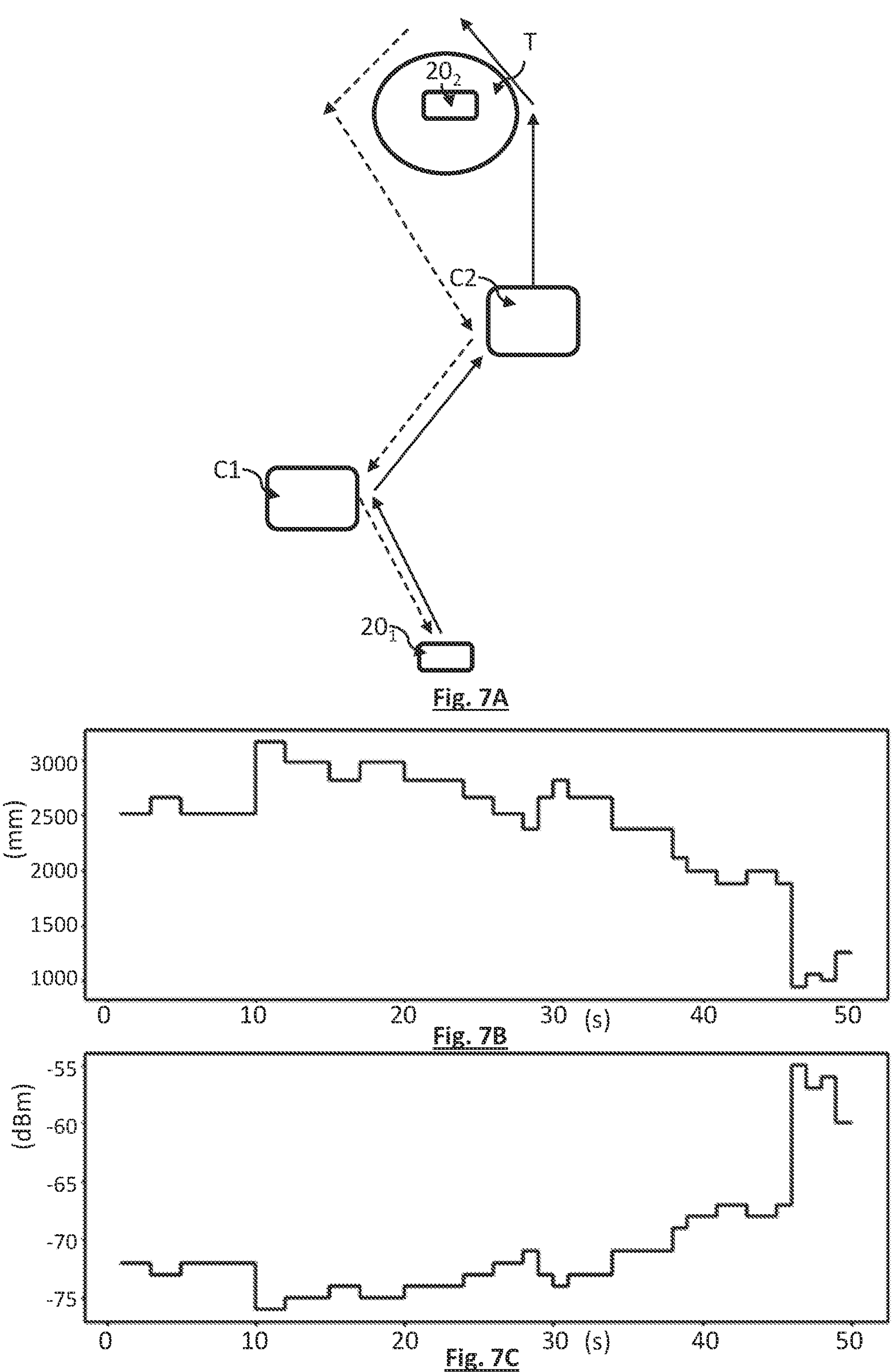
FIG. 7A illustrates a path of a user in an environment comprising two beacons referenced $\mathbf{20}_1$ and $\mathbf{20}_2$.
FIG. 7B shows the estimated distance between the mobile module worn by the user and the beacon $\mathbf{20}_1$. The ordinate axis corresponds to the distance (unit: mm). The abscissa axis corresponds to the time (unit: second)
FIG. 7C shows the power of a signal transmitted by the beacon $\mathbf{20}_1$ and received by the mobile module. The abscissa axis corresponds to the time (unit: seconds) and the ordinate axis corresponds to the power received by the mobile module (unit: dBm).

FIGS. 7A to 7F illustrate a distance measurement test, as well as measurements resulting from activity sensors 14 over a path followed by a user. During this test, the user has followed a path between two beacons $\mathbf{20}_1$, $\mathbf{20}_2$. The path extended between a beacon $\mathbf{20}_2$ and a table T, passing through two chairs C1, C2. The second beacon $\mathbf{20}_2$ was placed on the table T. Over the traveled path, the user sat on the chairs C1, C2, both on the outward and return leg. In FIG. 7A, the arrows in bold, dashed lines respectively show the outward journey, from the beacon $\mathbf{20}_1$ to the table T, as well as the return journey.

FIG. 7B shows the distance measured by the mobile module relative to the first beacon $\mathbf{20}_1$. The mobile module 10 was worn in front of the user. The masking effect of the user can be seen, which leads to overestimating of the distance relative to the first beacon $\mathbf{20}_1$ during the outward journey. The body of the user forms a screen leading to attenuation of the transmission signal $S_e$ between the beacon $\mathbf{20}_1$ and the mobile module, which induces the masking effect. This masking effect can be attenuated by using several beacons. FIG. 7C shows the power of the signal transmitted by the first beacon and received by the mobile module, as a function of time.

Figures 7D, 7E, 7F:
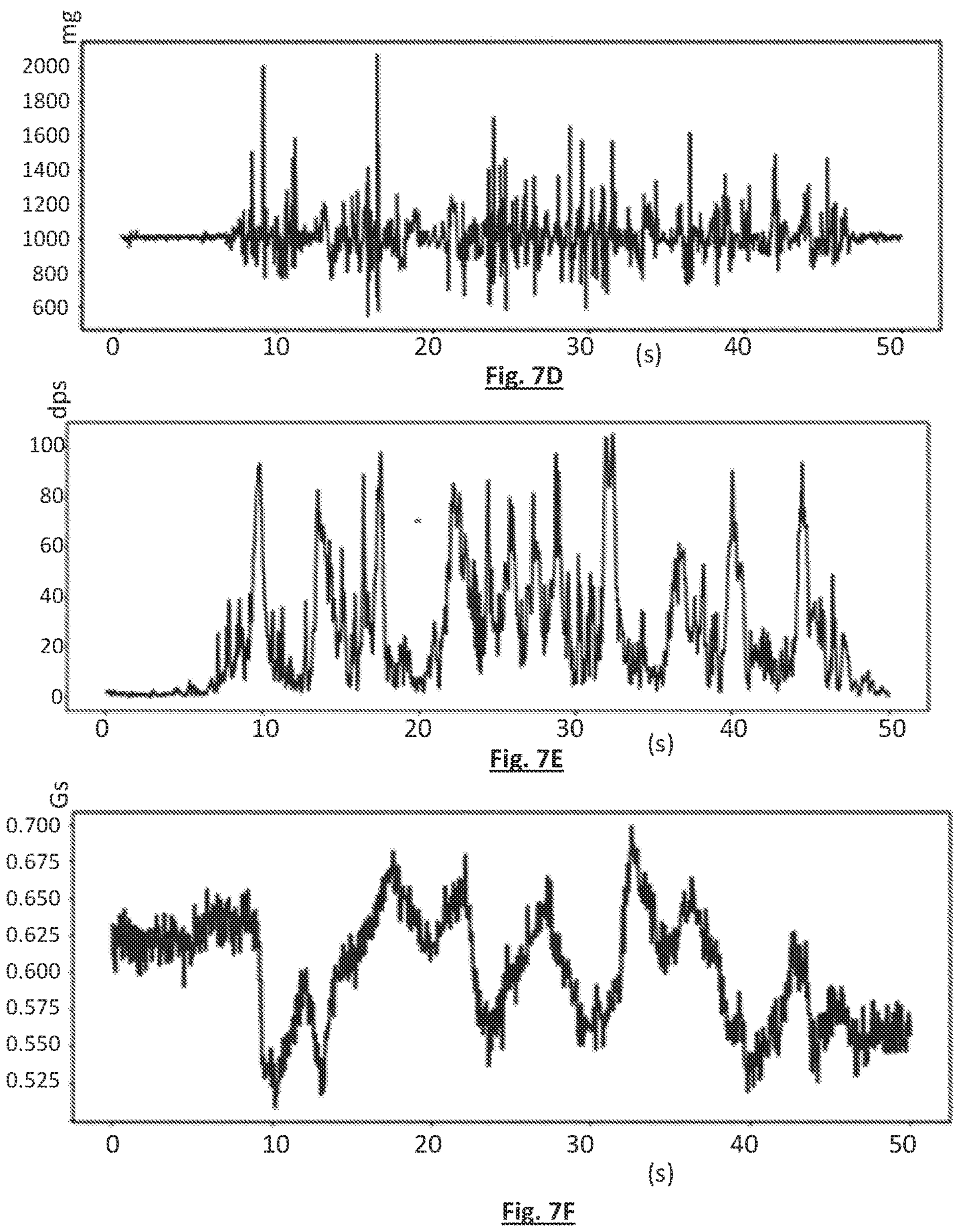
FIG. 7D, FIG. 7E, and FIG. 7F are measurements respectively resulting from an accelerometer, a gyroscope and a magnetometer integrated into the mobile module. In each figure, the ordinate axis represents the measured quantity (units: milli-g for FIG. 7D, degrees per second (dps) for FIG. 7E and Gauss (Gs) for FIG. 7F). In each of these figures, the abscissa axis corresponds to the time (unit: second).

FIGS. 7D, 7E and 7F show the signals measured by the accelerometer, the gyrometer and the magnetometer of the mobile module, as a function of time (abscissa axis: s). FIGS. 7A to 7F illustrate the ability of the device to simultaneously measure different distances, while measuring activity signals over a high time frequency.

Figure 8A:
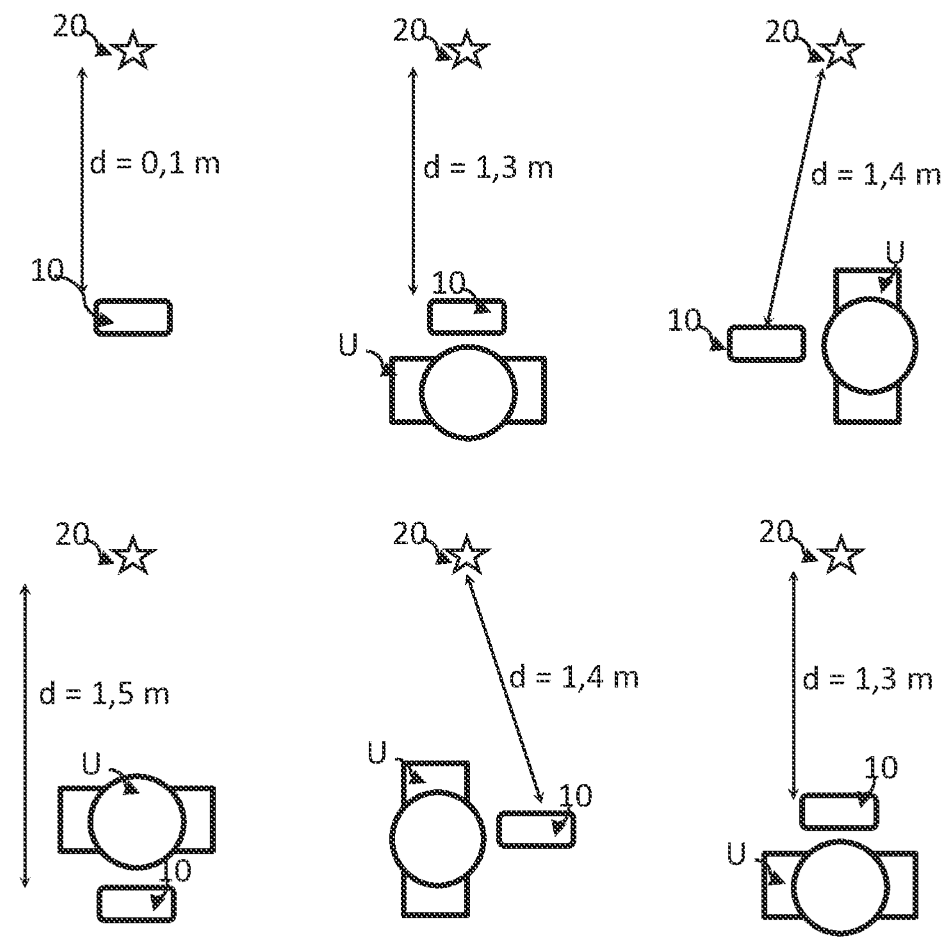
FIG. 8A illustrates various positions of a mobile module relative to a beacon, with a distance between the mobile module and the beacon having been measured in each position.
Figure 8B:
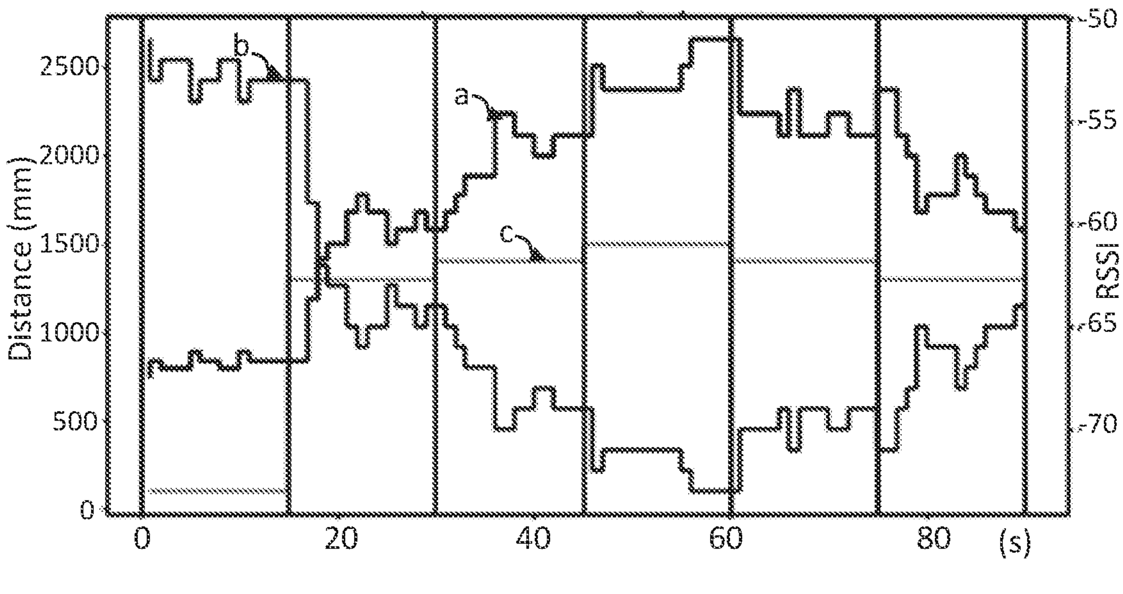
FIG. 8B shows the estimated distances between the mobile module and the beacon (curve a—left-hand ordinate axis—unit mm), as well as the power of the signal received by the mobile module (curve b—right-hand ordinate axis—unit dBs). Curve c represents the actual distances. The abscissa axis represents the time (unit seconds).

FIGS. 8A and 8B are an illustration of the masking effect induced by the body of the user. In FIG. 8A, the beacon is shown by a star. The user U, provided with the module, has performed an about turn, as shown in FIG. 8A, according to sequences lasting for 15 seconds. The double arrow represents the distance between the beacon and the mobile module 10 in each situation shown in FIG. 8A. In each configuration, the actual distance between the beacon and the mobile module is indicated. FIG. 8B shows the change in the RSSI power received by the mobile module (curve b) and the distance estimated from the RSSI power (curve a), by implementing the expression (1), and this is a function of time (abscissa axis—unit: s). FIG. 8B also shows the actual distance (curve c), with the distance being schematically shown by horizontal lines. These figures illustrate the masking effect of the user, in particular between 45 s and 60 s, which results in an overestimation of the distance, with the overestimation being approximately 1 meter. These measurements show that the distance between a beacon and the mobile module can be estimated with an uncertainty of 1 m. This is not an accurate measurement, but is sufficient for assessing a position of the user in a residence, and in particular for identifying the room occupied by the user. By respectively combining several distances between different beacons and the mobile module, the measurement uncertainty can be reduced, for example, by implementing a triangulation algorithm.

FIGS. 9A to 9F illustrate measured durations while a test user performed various tasks, with or without a 5 kg weight carried by the user, with this occurring in different rooms: room 1 and room 2. Room 1 included a first type of chair, and room 2 included a second type of chair. Carrying a weight corresponds to a simulation of a degradation in the state of health of the user. The step time was measured (period of the walking cycle), as was the time between a sitting position and a standing position (sit to stand time).

Figures 9A, 9B, 9C, 9D, 9E, 9F:
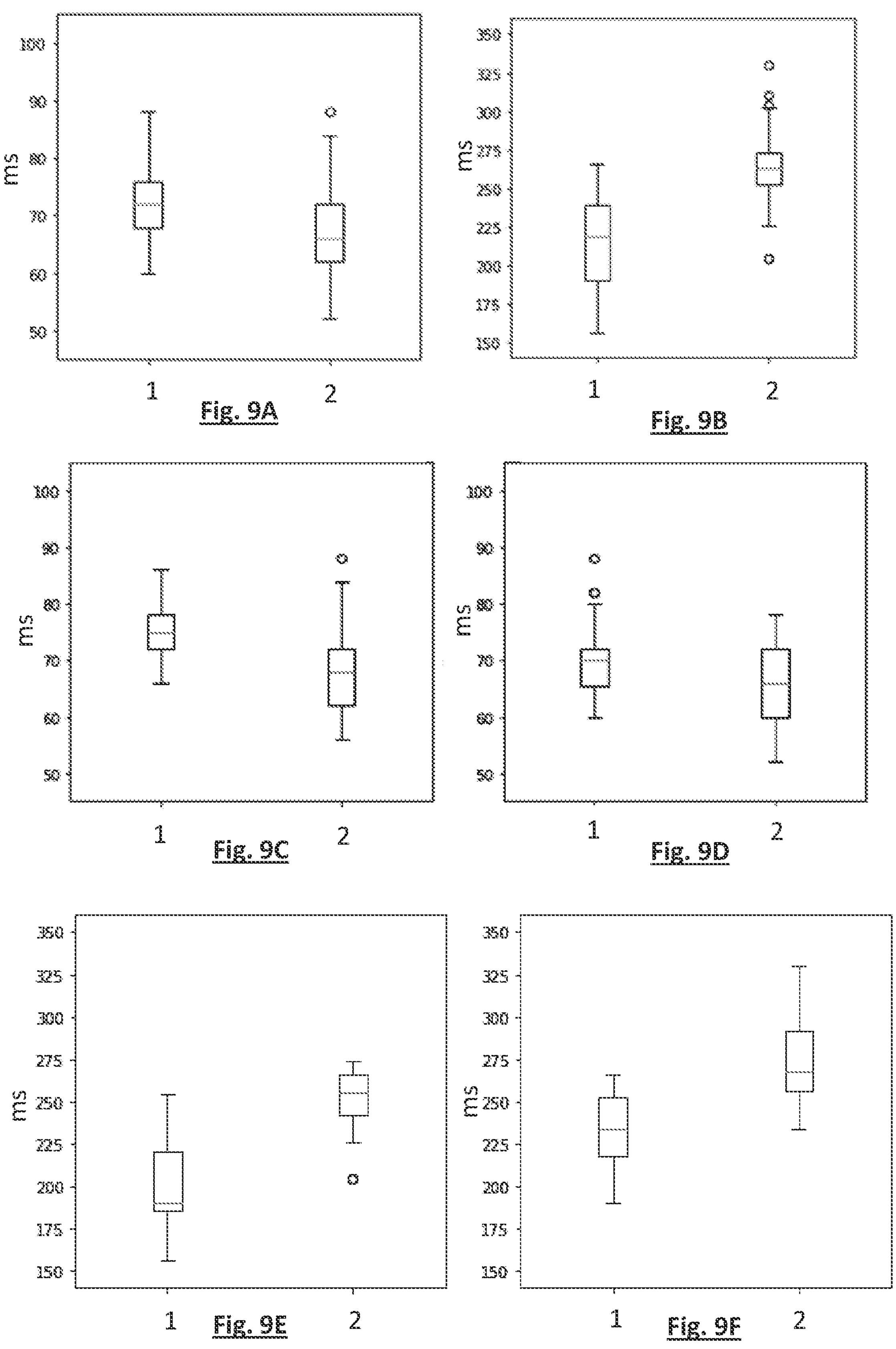
FIGS. 9A to 9F are box plots representing a variability of a duration of movements performed by a test user. The user has performed the movements normally or by carrying a 5 kg load. In each figure, the abscissa axis corresponds to the configuration of the user (1: normal configuration; 2: configuration carrying the load). The ordinate axis corresponds to the duration (unit: ms).

FIGS. 9A, 9C and 9D illustrate the measurements of the step time, while FIGS. 9B, 9E and 9F represent the measurements of the duration between the sitting position and the standing position. FIGS. 9A and 9B are established from non contextualized data: this is the set of measurements. FIGS. 9D to 9F are established from contextualized data, i.e., attached to position information of the user, in this case the room occupied by the user. FIGS. 9C and 9E correspond to room 1, while FIGS. 9D and 9F correspond to room 2. In each figure, the abscissa axis corresponds to the configuration of the user (1: normal configuration; 2: configuration whereby the user carries the 5 kg load). In each figure, the ordinate axis corresponds to the duration (unit: ins).

A statistical analysis of the data shown in FIGS. 9A to 9F shows the effect of contextualization of the data on the detection of an evolution of the state of health of the user. The main statistical results are shown in Tables 1 and 2 (for the step time—duration of the walking cycle), as well as 3 and 4 (for the sit to stand time—duration between the sitting position and the standing position). It can be seen that the variability of the measurements is lower when the measurements are contextualized. A consequence of the lower variability is a reduction in the size of the sample for determining the appearance of the symptom. The size of the sample is understood to mean the minimum size of the sample for characterizing the sample with a predetermined confidence level.

When the measurements are contextualized, the size of the sample is reduced, due to the lower variability of the measurements. This allows a change in the status of the user to be identified more precisely and earlier.

TABLE 1

| Step time (walking period) | Non-contextualized data No load (FIG. 9A) | Non-contextualized data With load (FIG. 9A) |
|---|---|---|
| Average | 71.94 | 66.27 |
| Variance | 6.22 | 7.31 |
| Cohen's d | 0.83 | |
| Sample size | 37 | 41 |

TABLE 2

| Step time (walking period) | Contextualized data - room 1 No load (FIG. 9C) | Contextualized data - room 1 With load (FIG. 9C) |
|---|---|---|
| Average | 75.26 | 68.7 |
| Variance | 4.88 | 7.99 |
| Cohen's d | 0.98 | |
| Sample size | 28 | 28 |

TABLE 3

| Sit to Stand (duration for standing) | Non-contextualized data No load (FIG. 9B) | Non-contextualized data With load (FIG. 9B) |
|---|---|---|
| Average | 216.1 | 262.4 |
| Variance | 30.53 | 25.66 |
| Cohen's d | 1.64 | |
| Sample size | 11 | 11 |

TABLE 4

| Sit to Stand (duration for sitting) | Contextualized data - room 1 No load (FIG. 9E) | Contextualized data - room 1 With load (FIG. 9E) |
|---|---|---|
| Average | 198.8 | 251.2 |
| Variance | 26.95 | 20.88 |
| Cohen's d | 2.17 | |
| Sample size | 7 | 7 |

Embodiments of the disclosure can be applied to other types of situations, some application examples of which will now be described.

The ability to correlate activity measurements with the presence of a third party can be used when studying autism: indeed, it was considered, for embodiments disclosed herein, that the activity of an autistic child varies when the child is alone or when the child is in the presence of a third party. Embodiments of the disclosure allow this to be contextualized, by assigning the presence of a third party to activity measurements as an ambience parameter.

During a convalescence, for example, following a viral episode, an individual can exhibit symptoms of fatigue, including reduced physical activity and difficulty in performing daily tasks. Embodiments of the disclosure allow the movement of a user between various rooms to be monitored, which allows the degree of fatigue of the user to be estimated on the basis of the data transmitted to the central unit.

For an elderly subject, embodiments of the disclosure allow beacons to be fixed on everyday objects, or in everyday rooms, which allows the activity of the individual to be monitored. The objects can be a household appliance, a shower, a bed, or the steering wheel of a car.

Within the context of clinical trials, embodiments of the disclosure allow the reactions of a participant to be identified and studied, for example, in terms of the heart rate, or of the temperature. Embodiments of the disclosure al low a significant reduction in the variability of the measurements carried out on the user, for example, the measurements representing a physiological status. Such a reduction in variability allows faster detection of the evolution of the status of the user who is the subject of the clinical trial.

Thus, the device according to embodiments of the disclosure can be implemented on different users simultaneously. This allows temporal ranges to be determined on each user, during which ranges the user is considered to be performing the same task. For example, it is possible to determine, for each user, time periods during which the user is seated, or lying down, or performing a particular motor skills task, for example, standing, sitting, or climbing a staircase, or walking in a straight line. Embodiments of the disclosure al low the selection of time ranges for each user, during which ranges the user performs the task. This allows data to be gathered that relates to the activity of each user, representing the considered task, during the time ranges selected for each user. During the selected time ranges, each user is considered to be performing the same task. As a result, the measured data have reduced variability. This allows more accurate analysis of the activity of the users, since the data relates to the activity of the user executing a specific task. It will be understood that this improves the statistical representativity of the measured signals (status signal and position signal), since it involves signals measured while each user performs the same task. The measured data are therefore more comparable. For example, data can be gathered that represents a movement in a straight line, or data that represents a transition from a standing position to a sitting or lying position, of users who have previously undergone the same surgical procedure, for example, the addition of a prosthesis. Embodiments of the disclosure allow data to be gathered for a large number of users performing the same task, in their natural environment, for example, in their home. This allows individual monitoring of each user or comparisons to be established between different users performing the same task.

The data gathered while the users are placed in the same context are more representative. They result in a more accurate statistical analysis, due to their lower variability.

One possible application relates to monitoring patients with a degenerative disorder, such as Parkinson's disease. Embodiments of the disclosure allow data to be gathered, for example, data characteristic of mobility, for different users placed in the same context. For example, the measured data (status signal, position signal) can be selected for users moving in a spacious room, for example, a corridor or a lounge. Thus, it is possible to gather contextualized data while each user moves in an environment they are familiar with. This is an alternative to the common monitoring methods, during which patients suffering from Parkinson's disease undergo tests in a hospital environment. Embodiments of the disclosure allow data gathering to be moved to the home of the user, while managing variability. Taking into account contextualized data allows patient-related data to be acquired on a daily basis. This allows better monitoring of the users. This can allow the effect of a treatment to be assessed, whether it is a desired effect or a secondary effect.

Furthermore, acquiring data relating to the activity of a user in a familiar environment can avoid any bias that may affect the measurements when the user is in a hospital environment. In this type of medical environment, the user may not behave naturally.

According to such an embodiment, the central unit 30 is configured to receive position signals $S_p$ and status signals $S_s$ of different users. The central unit 30 is then programmed to analyze the position signals and/or the status signals so as to select, for each user, measurement times during which each user undertakes a previously defined task. The selected measurement times define, for each user, various measurement time ranges. This allows different measurement time ranges to be defined for different users, during which time ranges the users are considered to be undertaking the same task. The data relating to the activity of the users, during the selected time ranges, are therefore comparable and are more suitable for statistical analysis by considering only the status signals $S_s$ and/or position signals $S_p$ transmitted by each user during each selected time range. It is understood that the time ranges assigned to a user can differ from the time ranges assigned to another user.

The central unit 30 then can be programmed to characterize the activity of each user when the user performs the predetermined task. According to this embodiment, the central unit 30 and the measuring device form a system for monitoring different users, with each user being equipped with a device 1 as described above.

Such an embodiment can be implemented by simultaneously considering different tasks of the user, and by selecting time ranges for each user that are respectively assigned to each task.

As mentioned above, most of the beacons 20 are fixedly distributed and form an array of beacons. According to one embodiment, at least one beacon, and preferably each beacon, is configured to estimate the distance separating it from one or more other beacons. Each beacon 20 is configured to transmit an identification signal comprising a digital identifier of the beacon. The power of the identification signal transmitted by a beacon 20, and detected by another beacon, allows a distance to be estimated between the two beacons. A beacon 20, or even each beacon, can be configured to transmit relative position data $S_{20}$ of other beacons to the mobile module 10, with the relative position data comprising:

- an identification of the other beacons, called neighboring beacons; and
- information representing the distance between the considered beacon and the neighboring beacons: this can be a power of the identification signal transmitted by each neighboring beacon or distances computed on the basis of the power of the identification signal.

The relative position data $S_{20}$ are contained in the transmission signal $S_e$ transmitted by each beacon 20 to the mobile module 10 during step 120.

The mobile module 10 receives, from at least one beacon 20, or from each beacon, the relative position data $S_{20}$ as defined above. The relative position data $S_{20}$ are transmitted to the central unit 30. Gathering relative position data $S_{20}$ by the central unit 30 allows a possible movement of a beacon 20 to be detected relative to a reference position that is previously recorded for the beacon. According to this embodiment, the central unit 30 has a reference map, according to which each beacon 20 occupies a reference position. The relative position data $S_{20}$ allows the distances between each beacon to be compared with reference distances, which correspond to the distances between the beacons when the beacons occupy their reference position. Such an embodiment allows a modification of a position of a beacon to be identified relative to the reference position. In such a case, the transmission signals $S_e$ transmitted by the beacon whose position has been modified are considered to be invalid or dubious. An action for checking the position of the beacon also can be initiated. Such an embodiment allows the reliability of the device to be improved, by ensuring that each beacon actually occupies a reference position that has been previously assigned thereto. According to this embodiment, the central unit 30 is programmed for:

- receiving data representing the relative position of the various beacons; and
- comparing, on the basis of the received data, the position of each beacon with the reference configuration according to which each beacon occupies the reference position that has been assigned thereto.

The reference configuration can be initialized during an initialization phase. According to this embodiment, the central unit and the measuring device form a user monitoring system.

Figure 10:
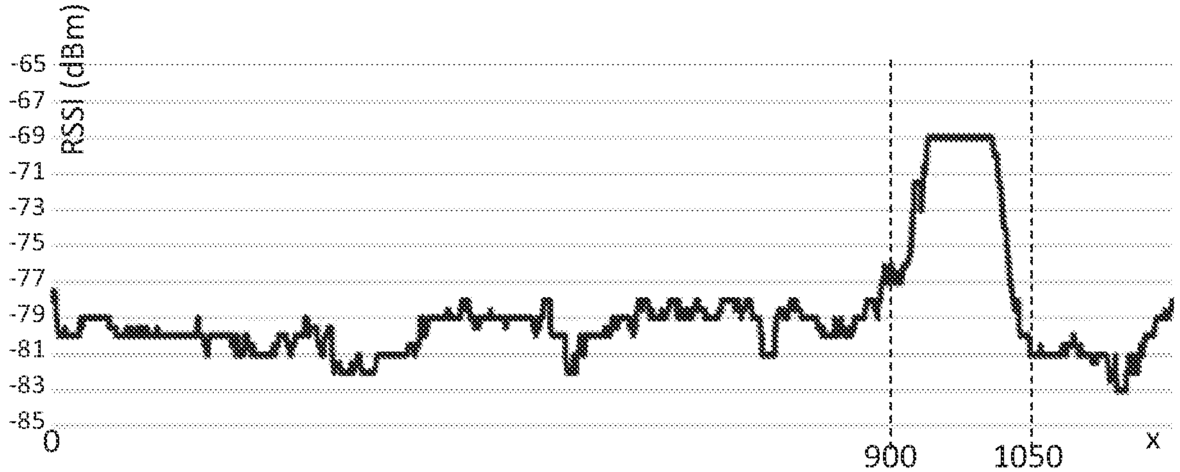
FIG. 10 represents a measurement of the distance between two beacons as a function of time.

FIG. 10 shows an experimental test, during which the distance between two beacons was measured as a function of time. The abscissa axis corresponds to the time, each increment x of the abscissa axis corresponds to 10 seconds, and the ordinate axis corresponds to the distance between the two beacons, expressed in the form of an RSSI power of the signal exchanged between the two beacons—unit: dBm. During this test, the distance was measured by a first beacon, which remained fixed. The distance was measured by taking into account a power of the identification signal transmitted by the second beacon, as described with reference to the expression (1). Before the x coordinate=900 and after the x coordinate=1,050, the distance between the two beacons was fixed and equal to 3.5 meters. Between x=900 and x=1,050, the second beacon was temporarily brought closer by a distance of 1 meter, which results in an increase in RSSI power.

According to one embodiment, during step 140, the communication between the mobile module 10 and the central unit 30 is carried out according to a protocol allowing transmission, by the mobile module, of data stored in the mobile module (notably the position signals $S_p$ and the status signals $S_s$ acquired as a function of time), and optionally data $S_{20}$ relating to the relative position of the beacons. The amount of data to be transmitted can be high, while monitoring of the user must be maintained.

Furthermore, the mobile module 10 must be configured to receive a transmission signal $S_e$ originating from the beacons 20 as regularly as possible. As previously indicated, the transmission signal $S_e$ transmitted by each beacon 20 comprises an identifier of the beacon. The power of the transmission signal allows the distance between the beacon 20 and the mobile module 10 to be estimated. Estimating the distance optionally takes into account the orientation of the beacon and the orientation of the mobile module, so as to compare the transmission patterns of the beacon and the reception patterns of the mobile module. The transmission signal $S_e$ transmitted by each beacon 20 can also comprise an ambience parameter, as well as relative position data $S_{20}$ of the neighboring beacons.

The mobile module 10 also must be configured to transmit the status signal $S_s$, the position signal $S_p$ and optionally the relative position data $S_{20}$ transmitted by one or more beacons 20 to the central unit 30. The transmission must be as regular as possible.

The use of a mobile module 10 that can simultaneously operate according to a transmission mode and a reception mode can be contemplated. However, this increases the cost and the power consumption of the mobile module. In order to limit the cost and consumption of the mobile module, a clever solution involves using a "single-mode" mobile module that can alternatively operate either in transmission mode or in reception mode. This assumes the implementation of a specific protocol alternately managing the transmission and the reception of the data by the mobile module.

It was considered, for embodiments disclosed herein, that the duration for receiving transmission signals $S_e$, transmitted by the beacons 20, is a few seconds, for example, 2 seconds. The duration for transmitting data ($S_s$, $S_p$, $S_{20}$) from the mobile module to the central unit 30 can be longer, for example, a few minutes. During the transmission period, the mobile module 10 cannot receive transmission signals $S_e$ transmitted by beacons 20. The position information of the user in the environment, allowing contextualization of the activity of the user, is lost. Therefore, the following needs to be managed for the mobile module 10:

- short periods for receiving the transmission signals $S_e$, transmitted by the beacons 20, which periods must be as frequent as possible, for example, every second, and, more generally, several times per minute. The transmission signals $S_e$ are received by the wireless connection unit 11; and
- long periods for transmitting data to the central unit 30, and which can be performed at a slower rate than the reception of the transmission signals $S_e$, for example, one or more times per hour. The data is transmitted by the transmission unit 16.

It is understood that, when the nomadic device 10 is a single-mode device, the transmission and reception periods cannot be performed simultaneously.

It is preferable for the effect of data transmission to the central unit to be limited to the frequency for receiving transmission signals $S_e$ from beacons. Furthermore, the mobile module 10 can be configured to transmit the position signal $S_p$, the status signal $S_s$ and any relative position data $S_{20}$ at a "slow" frequency, which is at least 10 times slower or at least 100 times slower than the frequency for receiving transmission signals $S_e$ transmitted by the beacons 20.

The protocol for transmitting/receiving the data by the mobile module 10 can be configured such that, during each transmission sequence to the central unit 30, when the transmission duration exceeds a predetermined duration, for example, 30 seconds or 1 minute, the transmission is interrupted. Following the interruption of the transmission, the mobile module 10 switches from the transmission mode to the reception mode, so as to receive transmission signals $S_e$ transmitted by the beacons. After at least one reception sequence, the mobile module 10 switches from the reception mode to the transmission mode, so that the transmission of data ($S_s$, $S_p$, $S_{20}$) to the central unit can continue. In general, when the transmission of the data to the central unit exceeds the predetermined duration, the data transmission is interrupted so as to allow transmission signals $S_e$ originating from the beacons to be received. Following the reception of the data, the transmission of data to the central unit 30 is resumed.

According to this protocol, the transmission of data is divided into different time segments, so as to allow reception of at least one transmission signal $S_e$ transmitted by at least one beacon 20 between two consecutive time segments. The duration of each time segment can be a few seconds or a few tens of seconds.

Embodiments of the disclosure also can be used in the work environment, in particular for monitoring the activity of operators, so as to optimize journeys, or for monitoring isolated workers. The aim then can be to improve the safety of the operators.

The invention claimed is:

1. A device for monitoring a status of a user, with the user occupying an environment, the device comprising:

- a mobile module, configured to be worn by the user; and
- beacons, distributed in the environment, configured to send a transmission signal to the mobile module via a short-range wireless connection;

the mobile module comprising:

- a short-range wireless connection unit, configured to receive at least one transmission signal transmitted by at least one beacon;
- a range-finding unit, configured to estimate, at different measurement times, a distance between the mobile module and the at least one beacon whose transmission signal is received by the mobile module;
- at least one activity sensor of the user, configured to establish an activity signal representing an activity of the user at each measurement time;

wherein the device further comprises:

- a processing unit, configured to establish a position signal as a function of at least one distance estimated by the range-finding unit, at each measurement time, with the position signal representing a position of the user relative to the environment; and
- a transmission unit, configured to transmit the position signal and the activity signal to a central unit;

wherein the central unit is configured to:

- determine the status of the user, from both of the position signal and the activity signal, the status of the user being selected from among a plurality of predetermined statuses, the status of the user being at least one of:
  - a physical activity undertaken by the user at the measurement time;
  - a stress status of the user at the measurement time; and
  - a physiological status of the user at the measurement time; and
- characterize the status of the user.

2. The device of claim 1, wherein characterizing the status is one of:

- estimating a duration of the status; and
- analyzing at least one activity signal of the user during the status.

3. The device of claim 1, wherein at least one beacon is a privacy beacon, the device being programmed such that when the mobile module is arranged at a distance from the privacy beacon that is below a threshold distance, no position signal and no activity signal is transmitted to the central unit.

4. The device of claim 1, wherein the activity sensor comprises at least:

- a motion sensor; and/or
- a cardiac activity sensor; and/or
- a muscle activity sensor; and/or
- a brain activity sensor; and/or
- a blood pressure sensor; and/or
- an analyte sensor.

5. The device of claim 1, wherein the range-finding unit is configured to estimate a distance between the mobile module and the at least one beacon as a function of the strength or the power of the transmission signal sent by the beacon to the mobile module.

6. The device of claim 5, wherein:

the mobile module comprises an orientation unit, configured to estimate an orientation of the mobile module; and the range-finding unit takes into account an orientation of the mobile module to estimate the distance of the mobile module and each beacon whose transmission signal is received by the mobile module.

7. The device of claim 1, wherein the range-finding unit is configured to estimate several distances between the mobile module and respectively several beacons as a function of transmission signals respectively transmitted by each beacon to the mobile module.

8. The device of claim 7, wherein the processing unit is configured such that the position signal corresponds to a position of the mobile module relative to several beacons.

9. The device of claim 1, wherein the short-range wireless connection is a connection with a range of less than 50 meters or 30 meters.

10. The device of claim 1, wherein:

the at least one beacon comprises an ambience sensor, configured to measure a temperature and/or a sound level and/or a light level;

the at least one beacon is configured to transmit an ambience signal to the mobile module that is dependent on the measurement carried out by the ambience sensor; and the processing unit is programmed to assign an ambience level to each status signal that is dependent on the ambience signal.

11. The device of claim 1, wherein:

the at least one beacon is configured to receive an identification signal transmitted by at least one other beacon, with the power of the identification signal being dependent on a distance between the two beacons;

the at least one beacon is configured to transmit a transmission signal comprising a relative position signal, with the relative position signal being determined from a power of each identification signal received by the at least one other beacon; and the mobile module is configured to transmit the relative position signal to the processing unit.

12. The device of claim 1, wherein:

the processing unit and transmission unit are enclosed within the mobile module;

the mobile module is configured to switch between:

a reception mode, in which the short-range wireless connection unit receives at least one transmission signal transmitted by at least one beacon; and a transmission mode, wherein the transmission unit transmits the activity signal and/or the position signal, at each measurement time, to the central unit; and the mobile module is configured such that:

when the duration of the transmission mode exceeds a predetermined duration, the transmission mode is interrupted, so as to allow switching from the transmission mode to the reception mode; and following the reception of at least one transmission signal, the module switches from the reception mode to the transmission mode, so as to continue the transmission to the central unit.

13. A method for monitoring the status of the user of the device of claim 1, wherein the user is placed in the environment, with the user wearing the mobile module of the device, with several beacons of the device being distributed in the environment, the method comprising, for at least one measurement time:

a) measuring an activity of the user, using at least one activity sensor of the mobile module, and generating an activity signal therefrom;

b) estimating a distance between the mobile module and at least one beacon;

c) determining, from the distance or from each distance estimated in b), a position signal representing a position of the user in the environment;

d) determining, with a central unit, a status of the user, from both of the position signal and the activity signal, the status of the user being selected from among a plurality of predetermined statuses, the status of the user representing at least one of:

a physical activity undertaken by the user at the measurement time;

a stress status of the user at the measurement time; and a physiological status of the user at the measurement time; and e) characterizing, with the central unit, the status of the user.

14. The method of claim 13, wherein characterizing the status of the user is one of:

estimating a duration of the status; and analysing at least one activity signal of the user during the status.

15. The method of claim 13, wherein the at least one beacon is a privacy beacon, with the device being programmed such that when the mobile module is placed at a distance from the privacy beacon that is below a threshold distance, no activity signal and no position signal is transmitted to the central unit.

16. The method of claim 13, wherein the at least one beacon is fixed in the environment.

17. The method of claim 13, wherein the at least one beacon is worn by a third party, other than the user.

18. The method of claim 13, wherein:

the environment comprises an object, likely to be in contact with the user or handled by at least one user; and the at least one beacon is attached to the object.

19. A method for monitoring a status of a plurality of users, with each user of the plurality of users using the device of claim 1, the each user being placed in an environment, the each user wearing the mobile module of the device, with several beacons of the device being distributed in the environment of the each user, the method comprising, for the each user, at different measurement times:

a) measuring an activity of the each user, using at least one activity sensor of the mobile module, and generating an activity signal therefrom;

b) estimating a distance between the mobile module and at least one beacon;

c) determining, from the distance or from each distance estimated in b), a position signal representing a position of the each user in the environment;

d) determining a status of the each user, from both of the position signal and the activity signal, the status of the each user being selected from among a plurality of predetermined statuses, the status of the each user representing at least one of:

a physical activity undertaken by the each user at the measurement time;

a stress status of the each user at the measurement time; and a physiological status of the each user at the measurement time;

e) characterizing, with the central unit, the status of the each user;

the method comprising, after carrying out steps a) to e), for the plurality of users, and at different measurement times:

taking into account a predetermined task;

selecting, for the each user, measurement times during which the status of the each user corresponds to said task, with the measurement times selected for the each user forming at least one time range specific to the each user; and characterizing the activity of the each user during one time range specific to the each user.

20. The method of claim 19, wherein characterizing the status is one of:

estimating a duration of the status; and analysing at least one activity signal of the each user during the status.

* * * * *